United States Patent [19]

Halle et al.

[11] 4,279,831

[45] Jul. 21, 1981

[54] 2-CHLORO-2-ALKYL SUBSTITUTED ASYMMETRICAL DIACYL PEROXIDES

[75] Inventors: Reidar Halle, Novato; David Peterson, Hercules; Roger N. Lewis, Martinez, all of Calif.

[73] Assignee: Argus Chemical Corporation, Brooklyn, N.Y.

[21] Appl. No.: 65,410

[22] Filed: Aug. 10, 1979

[51] Int. Cl.$^3$ .............................................. C07C 179/14
[52] U.S. Cl. ............................. 260/453 RZ; 526/231
[58] Field of Search .................................. 260/453 RZ

[56] References Cited

U.S. PATENT DOCUMENTS

| | | | |
|---|---|---|---|
| 3,502,701 | 3/1970 | Lewis et al. | 568/560 |
| 3,527,743 | 9/1970 | Friedman | 568/560 |
| 3,652,681 | 3/1972 | Wood | 568/560 |
| 3,687,867 | 8/1972 | Lewis et al. | 568/560 |
| 3,763,128 | 10/1973 | Lewis et al. | 568/560 |
| 3,932,372 | 1/1976 | Lewis et al. | 568/560 |
| 4,032,605 | 6/1977 | Wood | 568/560 |
| 4,102,815 | 7/1978 | Friedman et al. | 568/560 |
| 4,107,419 | 8/1978 | Friedman et al. | 568/560 |

OTHER PUBLICATIONS

J. Org. Chem. 40, 3420, (1975).
J. Org. Chem. 40, 3427, (1975).
Zh. Org. Khim, 6, 466, (1970).
Chem. Abs. 72, 1970, 131998r.

*Primary Examiner*—Henry R. Jiles
*Assistant Examiner*—Robert C. Whittenbaugh
*Attorney, Agent, or Firm*—Townsend and Townsend

[57] ABSTRACT

Dialkyl diacyl peroxides in which the alpha carbon atom of one of the alkyl groups is secondary and substituted by chloro and alkyl. The compounds are useful as polymerization initiators of ethylenically unsaturated monomers such as vinyl chloride.

10 Claims, No Drawings

2-CHLORO-2-ALKYL SUBSTITUTED ASYMMETRICAL DIACYL PEROXIDES

BACKGROUND OF THE INVENTION

1. Field of the Invention

This invention relates to organic peroxide polymerization initiators and their use in the polymerization of monomers and comonomers. More particularly, it relates to diacyl peroxides having chloro and alkyl substitution on one of the carbon atoms bonded to a carbonyl group.

2. Brief Description of the Prior Art

The Russian paper Zh. Org. Khim., 1970, 6(3), 446-8 (Russ) as reported in Chem. Abstracts, Vol. 72, 1970, p. 297, 131998r, describes the preparation of the symmetrical diacyl peroxide, di(2-chloro-2-methyl) propionyl peroxide and the aromatic diacyl peroxide, benzoyl 2-chloro-2-methyl propionyl peroxide.

2-chloro substituted diacyl peroxides and their use as polymerization initiators are disclosed in U.S. Pat. Nos. 4,032,605 and 3,652,681. 2-alkyl substituted diacyl peroxides and their use as polymerization initiators are disclosed in U.S. Pat. Nos. 3,527,743 and 3,502,701.

The use of diacyl peroxides as part of a coinitiator system for use as polymerization initiators is disclosed in U.S. Pat. Nos. 4,107,419, 4,102,815, 3,932,372, 3,687,867 and 3,763,128.

SUMMARY OF THE INVENTION

The present invention provides organic peroxides of the formula:

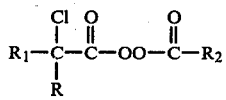

where R and $R_1$ are alkyl and which together contain up to about 10 carbon atoms, and $R_2$ is an alkyl group having up to about 18 carbon atoms.

In the preferred embodiment R and $R_1$ are methyl, while good results are also obtained when R is selected from methyl and ethyl and $R_1$ has up to about 7 carbon atoms. A preferred group of compounds is also obtained when $R_2$ has up to about 11 carbon atoms.

The new compounds of this invention have utility as polymerization initiators for monomers and comonomers having ethylenic unsaturation. Preferably, the monomer polymerized will be selected from vinyl chloride, ethylene, styrene and methyl methacrylate, and the comonomers will preferably be vinyl chloride and vinyl acetate. Use of the present compositions for the polymerization of such systems provides the advantages of permitting effective conversion of monomer to polymer at relatively low temperatures. For example, conversion of vinyl chloride to polymer can be effectively accomplished at temperatures of less than about 40° C. and generally much lower, such as temperatures of less than about 35° C., or even less than about 25° C.

The present initiators also may be used as advantageously in a co-initiator system because of their ability to rapidly initiate polymerization in a short period of time. Thus, they may be employed together with different organic peroxides which are slower in commencing initiation of polymerization but which remain effective for longer periods of time to thereby achieve high overall yield of polymer.

DESCRIPTION OF THE PREFERRED EMBODIMENT

The compositions of the present invention are prepared by reacting a corresponding acid chloride with a peracid in the presence of base, according to the following formula in which R, $R_1$ and $R_2$ have the definitions above given:

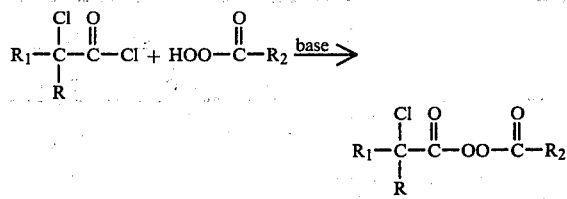

The following examples will illustrate the above reaction.

The acids were alpha-chlorinated and converted to acid chlorides in one pot according to the procedure reported in J. Organic Chem. 40, 3420 (1975). The following is an example of a typical synthesis:

EXAMPLE 1

Preparation of 2-Chloro-2-Ethyl Hexanoyl Chloride

To 100 g of 2-ethylhexanoic acid (0.693 moles) was added 247.5 g of thionyl chloride (2.080 moles) over 30 minutes and then the solution was heated at 70° C. for 2 hours. To the cooled solution was added 185.2 g of N-chloro succinimide (1.387 moles), 165.0 g of thionyl chloride (1.387 moles) and 2.0 ml of concentrated HCl. The mixture was heated at 80° C. for 2 hours, after which time there was no more apparent $Cl_2$ gas being given off. The mixture was cooled and filtered. The filtrate was distilled at atmospheric pressure to remove the $SOCl_2$ and then distilled to give a major fraction at 95°-105° C. (20 mm) weighing 28.00 g. Purity was determined by GLC analysis. Purity (area %) was 85.7%; yield was 17.6%. The product had a satisfactory IR, and the NMR showed no detectable extra chlorination.

GLC analysis was done on a Hewlett-Packard 5830A Gas Chromatograph under the following conditions: ⅛"×6" ss column containing 10% DC200 on 80/100 Varaport 30; temperature 1=125° C., time 1-5, rate - 15°/min.; temperature 2=200° C.; injector temperature=200° C.; FID temperature=250° C.; chart speed=1; and flow rate=30 cc/min.

The synthesis of various other 2-chloro-2-alkyl substituted acid chlorides is given in Table I.

The following is an example of a typical synthesis of a 2-chloro-2-alkyl substituted asymmetrical diacyl peroxide:

EXAMPLE 2

Preparation of Lauroyl-2-chloro-2-ethylhexanoyl peroxide (LCEHP)

To 5.00 g of 98.7% perlauric acid (0.023 moles, 1.0 eg), 18.00 g of DMP, and 60 ml of anhydrous acetone at −15° C. was added 2.01 g of pyridine (0.025 moles, 1.1 eq). Then 4.56 g of 2-chloro-2-ethylhexanoyl chloride (85.7%) (0.025 moles, 1.0 eq) was added over 15 minutes. The reaction was stirred at −15° C. for 30 minutes and then partitioned between 100 ml of cold ether and 50 ml of cold saturated NaHCO₃ solution. The organic layer was washed with 50 ml of cold 5% HCl solution, 50 ml of cold saturated NaHCO₃ solution, dried (MgSO₄), and evaporated to leave the product weighing 22.66 g. Product A.O. analysis: theory, 4.34; found 1.07; 24.6% pure as a solution in DMP; 65.3% yield.

The synthesis data of various 2-chloro-2-alkyl diacyl peroxides is given in Table II. The compounds were prepared by the above procedures substituting appropriate acid chlorides and peracids.

TABLE I
SYNTHESIS OF VARIOUS 2-CHLORO-2-ALKYL SUBSTITUTED ACID CHLORIDES

| | Acid Chloride | % Wt Purity (Area by GLC) | % Yield |
|---|---|---|---|
| 1. | 2-Chloro-2-ethyl butyryl chloride | 96.5 | 46.4 |
| 2. | 2-Chloro-2-methyl pentanoyl chloride | 93.2 | 20.1 |
| 3. | 2-Chloro-2-methyl propionyl chloride | 92.5 | 10.9 |

As mentioned, the present diacyl peroxides may be utilized to initiate the polymerization of ethylenically unsaturated monomers. Such polymerization is illustrated by the conversion of vinyl chloride monomer to polyvinyl chloride.

EXAMPLE 3

Vinyl Chloride Polymerizations

Suspension polymerizations were performed in 6 fluid ounce size pop bottles using uninhibited monomer in a constant temperature bath with a mixing speed of 42 rpm. Duplicate bottles were analyzed at each polymerization time interval. Bottles were frozen before venting off excess monomer. The weight ratio of water to vinyl chloride monomer was 2.5. The aqueous suspension solution in each bottle contained 0.30 g Dow Methocel K35, 35 cps, per 100 g of vinyl chloride monomer.

The results of the polymerizations at 25° C. are shown in Table III, the results at 40° C. in Table IV, and the results at 50° C. in Table V.

TABLE III
COMPARISON OF VINYL CHLORIDE POLYMERIZATIONS WITH VARIOUS 2-CHLORO-2-ALKYL SUBSTITUTED ASYMMETRICAL DIACYL PEROXIDES AT 25° C.

| | Diacyl Peroxides | % Wt Used | Moles ($\times 10^{-4}$)/ 100g VCM | Time, Hrs. | 1.5 | 3.5 | 5.5 | 7.0 |
|---|---|---|---|---|---|---|---|---|
| | | | | | % Conversion[1] | | | |
| 1. | BCEHP | 0.41 | 13.55 | | | | | 5.9 |
| 2. | ACEHP | 0.32 | 13.55 | | | | | 38.7 |
| 3. | PrCMPrP | 0.26 | 13.55 | | 17.2 | 39.7 | 77.5 | 82.4[2] |
| 4. | LCEHP | 0.50 | 13.55 | | | | | 49.2 |
| 5. | LCMPtP | 0.47 | 13.55 | | 29.7[3] | 55.6[3] | 68.8[3] | 76.1[3] |
| 6. | LCMPrP | 0.43 | 13.55 | | 44.4[3] | 62.4[3] | 79.3 | 89.1 |
| 7. | LCEBP | 0.47 | 13.55 | | | | | 50.3[3] |

[1]All values are the average of 2 runs unless otherwise indicated
[2]Single bottle value
[3]Average value from 3 runs

TABLE II
SYNTHESIS OF VARIOUS 2-CHLORO-2-ALKYL SUBSTITUTED ASYMMETRICAL DIACYL PEROXIDES

| | Diacyl Peroxide | MW | TAO | AO | % Wt Purity | % Wt Yield |
|---|---|---|---|---|---|---|
| 1. | Lauroyl 2-chloro-2-ethyl hexanoyl peroxide (LCEHP) | 386.89 | 4.34 | 1.07 | 24.6 | 65.3 |
| 2. | Lauroyl 2-chloro-2-methyl pentanoyl peroxide (LCMPtP) | 348.82 | 4.59 | 1.04 | 22.7 | 82.5 |
| 3. | Lauroyl 2-chloro-2-methyl propionyl peroxide (LCMPrP) | 320.79 | 4.99 | 1.20 | 24.1 | 75.1 |
| 4. | Lauroyl 2-chloro-2-ethyl butyryl peroxide (LCEBP) | 348.82 | 4.59 | 0.75 | 16.4 | 77.4 |
| 5. | Benzoyl 2-chloro-2-ethyl hexanoyl peroxide (BCEHP) | 298.76 | 5.36 | 0.95 | 17.7 | 62.1 |
| 6. | Propionyl 2-chloro-2-methyl propionyl peroxide (PrCMPrP) | 194.62 | 8.22 | 2.08 | 25.3 | 89.6 |
| 7. | Acetyl 2-chloro-2-ethyl hexanoyl peroxide (ACEHP) | 328.70 | 6.70 | 1.83 | 27.3 | 81.1 |

TABLE IV
COMPARISON OF VINYL CHLORIDE POLYMERIZATIONS WITH VARIOUS 2-CHLORO-2-ALKYL SUBSTITUTED ASYMMETRICAL DIACYL PEROXIDES AT 40° C.

| | Diacyl Peroxides | % Wt Used | Moles ($\times 10^{-4}$)/ 100g VCM | Time, Hrs. | 1.5 | 3.5 | 5.5 | 7.0 |
|---|---|---|---|---|---|---|---|---|
| | | | | | % Conversion[1] | | | |
| 1. | BCEHP | 0.06 | 2.00 | | | | | 0.7 |
| | | 0.15 | 5.00 | | | | | 2.9 |
| 2. | ACEHP | 0.05 | 2.00 | | | | | 15.0 |
| | | 0.12 | 5.00 | | | | | 30.8[2] |
| | | 0.19 | 8.13 | | | | | 21.3[3] |
| 3. | PrCMPrP | 0.16 | 8.13 | | 48.8[3] | 48.4[3] | 51.3[3] | 52.5[3] |
| 4. | LCEHP | 0.07 | 2.00 | | | | | 5.4 |

TABLE IV-continued
COMPARISON OF VINYL CHLORIDE POLYMERIZATIONS WITH VARIOUS 2-CHLORO-2-ALKYL SUBSTITUTED ASYMMETRICAL DIACYL PEROXIDES AT 40° C.

| Diacyl Peroxides | % Wt Used | Moles ($\times 10^{-4}$)/ 100g VCM | Time, Hrs. | % Conversion[1] 1.5 | 3.5 | 5.5 | 7.0 |
|---|---|---|---|---|---|---|---|
| | | 0.30 | 8.13 | | | | 26.0[3] |
| 5. LCMPtP | 0.28 | 8.13 | | | | | 43.5[3] |
| 6. LCMPrP | 0.26 | 8.13 | | 44.3[3] | 58.6 | 63.1[3] | 65.2[3] |
| 7. LCEBP | 0.28 | 8.13 | | | | | 36.6[3] |

[1] All values are the average of 2 runs unless otherwise indicated
[2] Single bottle value
[3] Average value from 3 runs

TABLE V
VINYL CHLORIDE POLYMERIZATION WITH LAUROYL 2-CHLORO-2-METHYL PROPIONYL PEROXIDE AT 50° C.

| Diacyl Peroxide | % Wt Used | Moles ($\times 10^{-4}$)/ 100g VCM | % Conversion after 6 Hours |
|---|---|---|---|
| LCMPrP | 0.06 | 2.0 | 20.6[1] |
| | 0.11 | 3.5 | 30.7[1] |
| | 0.16 | 5.0 | 39.9[2] |

[1] Average value from 3 runs
[2] Average value from 2 runs

Aside from the use of the present diacyl peroxides, the practice of the polymerization methods of this invention is consistent with prior art procedures for initiating the polymerization of the monomers vinyl chloride, ethylene, styrene and methyl methacrylate, and the copolymerization of vinyl chloride and vinyl acetate. Thus, the present peroxides are added in amounts generally comparable to those previously used and will usually fall within the range of about 0.005% to 3% by weight of monomer content and more commonly about 0.01% to 0.5% by weight of the monomer content. For practical purposes the minimum amount of peroxide is added which will effectively initiate the polymerization of the monomer mass within the desired period of time. The usual conditions of temperature, pressure, solvents and the like used in the polymerization of these monomers and comonomers may be employed.

When the present peroxides are to be used as part of a co-initiator system, again the amounts and conditions of the prior art may be followed. In this regard the teachings of the above referenced patents disclosing co-initiator systems with diacyl peroxides are incorporated herein by reference. Thus, the weight ratio of diacyl peroxide to coperoxide will generally be about 3:1 to 1:3, preferably 1:2. The amount of the combined peroxides relative to monomers and comonomers is as indicated above. Similarly, temperatures and other process parameters are as disclosed above and discussed in the referenced prior art.

What is claimed is:

1. An organic peroxide of the formula:

$$R_1-\underset{\underset{R}{|}}{\overset{\overset{Cl}{|}}{C}}-\overset{\overset{O}{\|}}{C}-OO-\overset{\overset{O}{\|}}{C}-R_2$$

where R and $R_1$ are alkyl which together contain up to about 10 carbon atoms, and $R_2$ is an alkyl group having up to about 18 carbon atoms.

2. An organic peroxide in accordance with claim 1 wherein R and $R_1$ are methyl.

3. An organic peroxide in accordance with claim 1 or 2 wherein $R_2$ has up to about 11 carbon atoms.

4. An organic peroxide in accordance with claim 1 wherein R is selected from methyl and ethyl and $R_1$ has up to about 7 carbon atoms.

5. An organic peroxide in accordance with claim 1 wherein the peroxide is lauroyl 2-chloro-2-ethyl hexanoyl peroxide.

6. An organic peroxide in accordance with claim 1 wherein the peroxide is lauroyl 2-chloro-2-methyl pentanoyl peroxide.

7. An organic peroxide in accordance with claim 1 wherein the peroxide is lauroyl 2-chloro-2-methyl propionyl peroxide.

8. An organic peroxide in accordance with claim 1 wherein the peroxide is lauroyl 2-chloro-2-ethyl butyryl peroxide.

9. An organic peroxide in accordance with claim 1 wherein the peroxide is propionyl 2-chloro-2-methyl propionyl peroxide.

10. An organic peroxide in accordance with claim 1 wherein the peroxide is acetyl 2-chloro-2-ethyl hexanoyl peroxide.

* * * * *